(12) United States Patent
Sekellick et al.

(10) Patent No.: US 6,716,607 B1
(45) Date of Patent: *Apr. 6, 2004

(54) CHICKEN INTERFERON GENE AND NOVEL RECOMBINANT DNA

(75) Inventors: Margaret J. Sekellick, Storrs, CT (US); Philip I. Marcus, Storrs, CT (US); Anthony F. Ferrandino, West Hartford, CT (US)

(73) Assignee: University of Connecticut, Farmington, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/495,491

(22) Filed: Feb. 1, 2000

Related U.S. Application Data

(63) Continuation of application No. 08/235,402, filed on Apr. 28, 1994, now abandoned, which is a continuation-in-part of application No. 08/139,909, filed on Oct. 22, 1993, now Pat. No. 5,641,656.

(51) Int. Cl.⁷ .......................... C12P 21/04; C12N 15/63; C07H 21/04; C07K 1/00

(52) U.S. Cl. ................................ 435/69.51; 435/320.1; 435/455; 536/23.52; 536/24.31; 530/351

(58) Field of Search ................ 536/23.52, 24.31; 435/69.51, 91.1, 320.1, 455; 530/351

(56) References Cited

U.S. PATENT DOCUMENTS

| | | | |
|---|---|---|---|
| 5,641,656 A | * 6/1997 | Sekellick et al. | ........ 435/69.51 |
| 6,001,369 A | * 12/1999 | Cochran et al. | ......... 424/199.1 |
| 6,020,465 A | * 2/2000 | Sekellick et al. | ........... 530/351 |

OTHER PUBLICATIONS

Digby, M.R. & Lowenthal, J.W. J. Interferon Cytokine Res. 15:939–945, 1995.*
Tamai et al. Biochim. Biophys. Acta 1174:182–186, 1993.*
Sekellick et al. J. Interferon Res. 14:71–79, 1994.*
Rudinger, J. In: "Peptide hormones", (Parsons, J.A., ed.) University Park Press, Baltimore, 1976, pp. 1–7.*
Ngo et al. In: "The protein folding problem and tertiary structure prediction", (Merz, Jr. et al., eds) Birkhauser, Boston, 1994, pp. 491–495.*

* cited by examiner

*Primary Examiner*—David Guzo
*Assistant Examiner*—Quang Nguyen
(74) *Attorney, Agent, or Firm*—McCarter & English

(57) ABSTRACT

A chicken interferon gene coding for the amino acid sequence of SEQ ID NO:1 is disclosed. There is also disclosed a method of producing chicken interferon recombinantly, a method of isolating other non-mammalian interferon genes, a method of making a transgenic fowl having the chicken interferon gene incorporated therein, and method for delivery of the chicken interferon in the bird, such as by genetic immunization or aerosol. Expression of the gene coding for the amino acid sequence of SEQ ID NO:1 yields functional chicken interferon.

9 Claims, 1 Drawing Sheet

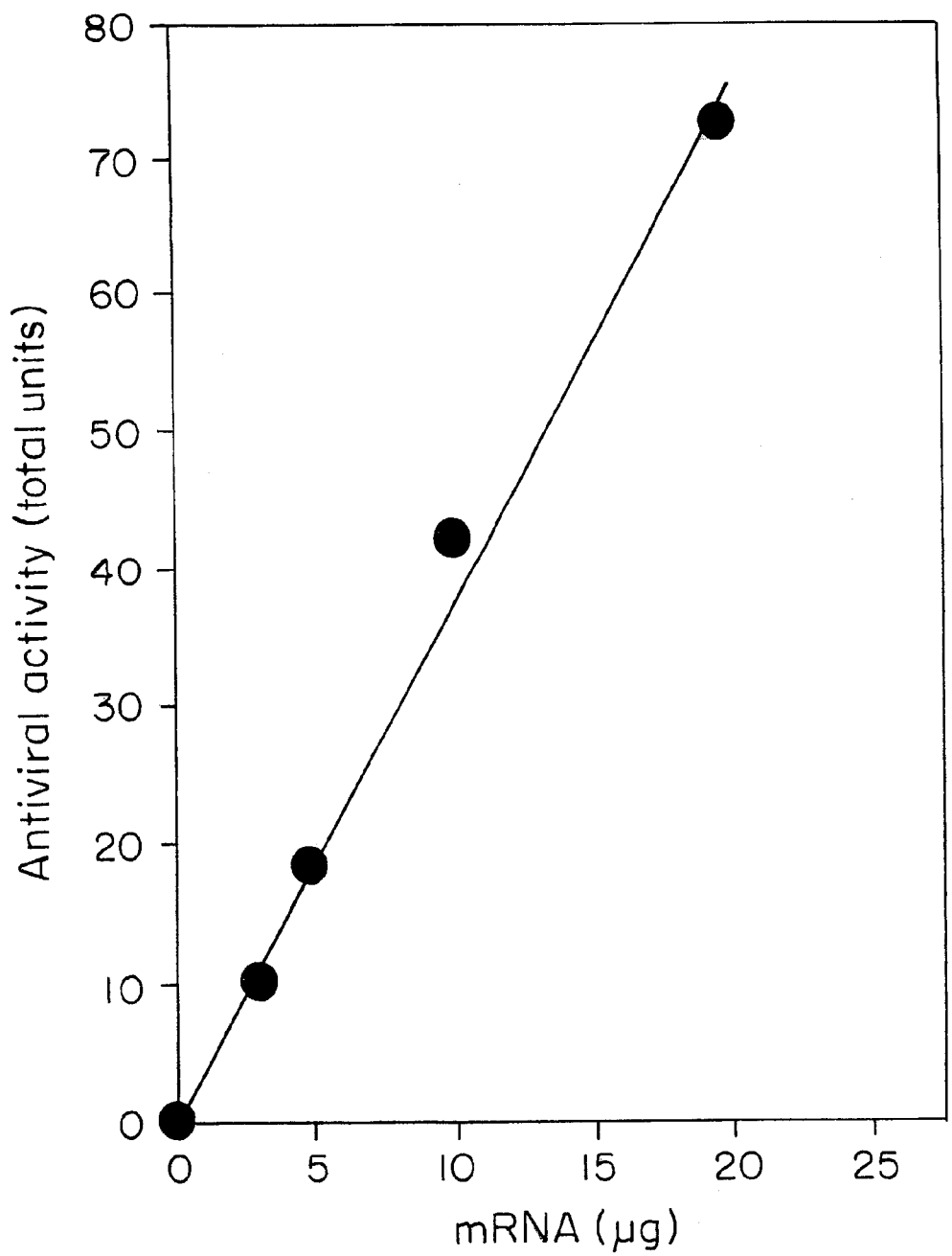

CHICKEN INTERFERON GENE AND NOVEL RECOMBINANT DNA

RELATED APPLICATION DATA

This is a continuation of application Ser. No. 08/235,402 filed Apr. 28, 1994, now abandoned which is a continuation-in-part of U.S. patent application Ser. No. 08/139,909 filed Oct. 22, 1993, now U.S. Pat. No. 5,641,656.

This application is related to U.S. Pat. No. 6,020,465 issued Feb. 1, 2000 on application Ser. No. 08/831,627 which is a continuation-in-part of application Ser. No. 08/139,900 filed Oct. 22, 1993 now U.S. Pat. No. 5,641,656 and to U.S. Pat. No. 5,885,567 issued Mar. 23, 1999 on application Ser. No. 308,821, which is a continuation-in-part of Ser. No. 235,402 abandoned which is a continuation-in-part of Ser. No. 139,902 filed Oct. 22, 1993 Now U.S. Pat. No. 5,641,656.

GOVERNMENT SUPPORT

The invention described herein was supported in whole or in part by Grant Number AI18381 from the National Institute of Allergy and Infectious Disease. The Government has certain rights in the invention.

BACKGROUND OF THE INVENTION

Mammalian interferons are valuable proteins useful in protecting and treating animals and humans from viral and other diseases, through the myriad actions of interferon (IFN). Marcus, *Encyclopedia of Virology*, 2:733–739 (1994); Krown et al., *Encyclopedia of Virology*, 2:739–745 (1994). The Food and Drug Administration has approved several uses of human IFN. Comparable studies with chickens and other avian species have been limited by the availability of chicken and avian IFN. Induction of avian interferon by virus has been successful in primary chick embryo cells "aged" in vitro, with yields of more than 100,000 units of IFN per $10^7$ cells (Sekellick and Marcus, *Methods in Enzymology*, 119:115–125 (1986)), and chicken interferon (ChIFN) has been shown specifically to protect chicken cells against the lethal action of several viruses (Marcus and Sekellick, *Virology*, 69:378–393 (1976); Marcus et al., *Journal of General Virology*, 64:2419–1431 (1983)).

In addition it is possible that some important parasitic diseases of chickens like that caused by Eimeria may be controllable by interferon through its effects on the immune system. Interferon is gaining increased attention as an antiparasitic agent, (Murray, *Journal Interferon Research*, 12:319–322 (1992)).

Many factors determine how much interferon is induced by a particular virus. These factors include its origin and passage history, the host cell, incubation conditions and time, and the multiplicity of infection. Stewart, "The Interferon System", 2nd. ed., Vienna:Springer-Verlag, pp 27–57; Marcus, Sekellick and Nichol, *Journal of Interferon Research*, 12:297–305 (1992).

SUMMARY OF THE INVENTION

This invention relates to isolated genes and recombinant DNA coding for non-mammalian interferon, processes for preparing and isolating them and methods of use therefor. The isolated gene preferably codes for avian, fish or reptile interferon. Preferred embodiments of avian interferon include fowl, such as but not limited to chickens, ostrich, emus, turkeys, ducks, and exotic birds, such as parrots, cockatoos, cockatiels, and other commercially valuable birds. The nucleotide sequence encoding chicken interferon is described herein.

This invention also relates to a method of producing recombinant chicken interferon which comprises culturing a transformed microorganism capable of producing chicken interferon, said microorganism having inserted therein a recombinant chicken interferon gene such as the DNA sequence of SEQ ID NO: 1, (GenBank Accession No. U07868) and recovering said chicken interferon. The amino acid sequence encoding the signal and mature IFN protein has been deduced and is described herein (SEQ ID NO: 1) and SEQ ID NO:6. The mature IFN protein has been shown to be biologically functional. The transformed microorganism employed may be any host cell or cells capable of producing the recombinant protein. Preferably the host cell is derived from a eukaryote, mammalian cell culture or prokaryote, with eukaryote (e.g., insect cells) or mammalian cell culture (e.g., CHO cells) being most preferred in order to achieve glycosylation. Active material has also been obtained from *E. coli*.

A cDNA probe is also described herein and comprises the nucleotide sequence of SEQ ID NO: 3. This cDNA probe, along with the cDNA of SEQ ID NO: 1, can be used to isolate and identify other non-mammalian interferon genes, such as other avian species, fish and reptiles, due to ancestral homology. A useful probe will comprise at least about a twenty base pair segment of the DNA sequence of SEQ ID NO: 1 which will bind to the complement of said sequence.

The invention also pertains to a plasmid comprising a) DNA sequence coding for non-mammalian interferon, preferably avian, fish and reptile interferon, most preferably chicken interferon, and b) a promoter sequence operably linked to said DNA sequence, preferably chicken metallothionein.

The novel plasmid constructs of this invention can be used to produce abundant quantities of recombinant interferon for administration to fowls and exotic birds, in order to prevent viral and/or parasitic infections. In another embodiment, interferon DNA can be introduced by genetic augmentation, i.e., genetic immunization. According to this method, DNA is introduced into the skin of the bird using a hand-held biolistic system (Sanford et al., *Technique* 3:3–16 (1992)) and serves as a template for manufacture of interferon. Tang et al., *Nature*, 356:152–154 (1992). Alternatively, the DNA and constructs containing the DNA of this invention can be used to produce transgenic fowl. The transgenic fowl would harbor an inducible plasmid for the transient expression of chicken interferon. Such transient expression would be induced at a time in the development of the fowl which would not retard growth but would provide protection against viral and/or parasitic infections.

This invention further pertains to transgenic fowl wherein its germ cells and/or somatic cells contain the recombinant DNA comprising an isolated avian interferon DNA introduced at an embryonic stage, and a method of making the same. Preferably, the recombinant DNA is substantially endogenous to the transgenic fowl, such as that coding for chicken interferon where the transgenic fowl is a transgenic chicken. In one embodiment, a promoter sequence heterologous to the chicken promoter can be operably linked to the recombinant DNA coding for chicken interferon in order to selectively induce expression of the interferon gene. An example of a heterologous promoter is the chicken metallothionein promoter which can be regulated by providing a source of metallic ions to the fowl. By this method, it is possible to treat or prevent viral and/or parasitic infection by inducing transcription of the DNA in the transgenic fowl.

BRIEF DESCRIPTION OF THE DRAWING

The Figure is a graph showing the relationship of antiviral activity produced by mouse L(Y) cells 20 hours after lipofectin-mediated transfection of chick embryo cells with mRNA transcribed from pCh132 DNA. The activity was neutralized completely with a monoclonal antibody to ChIFN. A preparation of mouse IFN which assayed at 65,000 units/ml on mouse L(Y) cells showed no antiviral activity on chick embryo cells.

DETAILED DESCRIPTION OF THE INVENTION

The first DNA nucleotide sequence and probe therefor that codes for a non-mammalian interferon, namely chicken interferon, are described herein. The nucleotide sequence coding the complete chicken interferon gene has been determined and is set forth in SEQ ID NO: 1. The sequence is 763 nucleotides in length and contains the following nucleotides starting at the 5' end: 54 bases of the 5' flanking sequence, 93 bases coding a 31 amino acid signal protein, 486 bases coding the mature chicken interferon protein, 3 bases for a stop signal, 127 bases comprising the 3' flanking region and a poly(A) tail.

The probe is the first DNA nucleotide sequence found to be specific for the chicken interferon messenger RNA (mRNA). A special system of "aged" primary chick embryo cells (Sekellick and Marcus, *Methods in Enzymology*, 119:115–125 (1985)), was used to induce the messenger RNA for chicken interferon. This chicken interferon probe shares less than 25% nucleotide sequence identity with reported mammalian interferon a and β species.

Primers were also designed to capture and synthesize a portion of the chicken interferon gene. PCR products were then produced, using these primers to amplify sequences from messenger RNA obtained from "aged" primary chick embryo cells, according to Sekellick and Marcus, "*Methods in Enzymology*", 19:115–125, (1986). A successful Northern blot using the chicken interferon DNA probe demonstrating the size of the interferon messenger RNA was obtained. The chicken interferon DNA probe is a 269 base sequence that includes two primer regions. The Northern blot was obtained using the chicken interferon DNA probe demonstrating an inducible messenger RNA with proper size and characteristics in response to control treatments such as cycloheximide, actinomycin D or 2-aminopurine in UV-avian reovirus infected "aged" primary chick embryo cells, as well as poly I-poly C treatment, and infection with vesicular stomatitis virus (VSV) serotype Indiana (IN) #22–20 and infection with VSV (IN) #22–25 in the same system.

The cDNA probe obtained by this method has the nucleotide sequence of SEQ ID No: 3. The probe comprises a 269 nucleotide sequence having a 5' primer region of 32 bases, a 3' primer region of 20 bases and a 217 base partial sequence of the chicken interferon gene. The probe can be manufactured by alternative processes well known in the art. Other useful probes, as discussed above, can be made in the same or similar manner. Preferred probes include those comprising at least about a 20 base pair segment of the DNA sequence of SEQ ID NO: 1 which will bind to the complement of the interferon gene. Preferably the base pair segment will be located in the region which corresponds to about nucleotide 487 to about nucleotide 633 of SEQ ID NO: 1. A highly conserved region is found at the 547–579 segment.

The probe can then be used in screening a chicken cDNA library, according to the methods described in detail below. In this procedure, 5 clones containing full-length coding regions and 1 truncated clone were isolated. The mRNA coding for chicken interferon can thereby successfully be obtained. Synthesis of cDNA from mRNA coding for chicken interferon can be performed by methods described in detail below.

The thus obtained cDNA can be incorporated into a cloning vehicle to obtain transformants. Cloning vehicles which can be used in this invention include plasmids, such as the SuperScript Plasmid System for cDNA Synthesis and Plasmid Cloning (available from GIBCO/BRL; Life Technologies, Inc.). The cDNA thus cloned is produced with Not I and Sal I termini for directional cloning into the Not I- Sal-I-Cut plasmid pSPORT I.

Using appropriate plasmids, or cloning vehicles, the DNA can be incorporated into an appropriate cell, such as a prokaryote or eukaryote, according to methods known in the art, such as *Current Protocols in Molecular Biology*, F. Ausubel, et al., (Eds.). The transformants are cultured to thereby express the cell protein. Confirmation of the expression of chicken interferon can be achieved by known assays. The expressed chicken interferon can be isolated from the culture according to known techniques, including, for example, Sekellick and Marcus Methods in Enzymol., 19:115–125 (1986). It has been shown herein that the expression of the isolated gene yields functional chicken interferon.

The amino acid sequence encoding the signal region and mature chicken interferon protein has been deduced (SEQ ID NO: 1). The mature protein has the amino acid sequence of SEQ ID NO: 2. Chicken interferon is a 20–30 KD glycosylated protein which is acid stable. The nonglycosylated molecule is an 18 KD protein. Directed mutation at the 4 potential N-glycosylation sites could lead to chicken interferon molecules with varying degrees of stability and enhanced biological activity. The 6 cysteine residues in the chicken interferon molecule provide the possibility of altering the number of potential disulfide bonds and, hence, stability properties of the molecule, as has been reported for mammalian interferons. Day et al., *Journal of Interferon Research*, 12:139–143 (1992). In this context, the acid labile form of chicken interferon reported by Yoshida and Marcus (*Journal of Interferon Research*, 19:461–468 (1990)), may reflect such transient changes.

In mammals, four families of type I interferon genes have been described, (e.g. interferon-alpha, beta, -omega and -tau) and one family of type II interferon (e.g. interferon-gamma). Southern analysis of genomic chicken DNA that have been carried out using probes described herein for chicken interferon indicates there may be only one chicken interferon gene. At the amino acid level, the chicken interferon gene shares only about 22% homology with all other type I mammalian interferons, i.e., interferons -alpha, -beta, -omega and -tau, and less than 3% homology with the type II mammalian interferon, i.e., interferon -gamma. It has been determined herein that chicken interferon is unusual in its content of 6 cysteine residues and 4 potential N-glycosylation sites. Because of its ancestral origin, the chicken interferon gene can be useful in detecting and isolating interferon genes of other nonmammalian species, for example, fish and reptiles.

Mammalian interferons have been engineered genetically to display more desirable traits, for example, altered host range and enhanced specific activity. Day et al., Ibid. Thus, using similar techniques it may be possible that the chicken interferon gene could be manipulated similarly.

Recombinant chicken interferon can then be administered to fowl, preferably chickens and exotic birds, in an amount effective to treat or prevent viral and/or parasitic infections and/or to enhance the immune system. Examples of avian viruses for which chicken interferon could be used to treat/prevent diseases caused thereby include but are not limited to orthomyxovirus (eg., influenza); paramyxovirus (eg., Newcastle disease virus); coronavirus (eg., infectious bronchitis); hepadnavirus (eg., hepatitis); poxvirus (eg., fowl pox); adenovirus (eg., adenovirus); retrovirus (eg., leukosis virus); herpesvirus (eg., Marek's disease). Parasitic infection such as that caused by Eimeria or other parasites which are controllable by interferon can also be treated/prevented using the recombinant interferon of this invention.

The interferon can be formulated into a veterinary preparation, for example, in semisolid or liquid form, which contains the recombinant chicken interferon, as an active ingredient, in admixture with suitable organic or inorganic carriers or excipients. The active ingredient may be compounded, for example, with the usual non-toxic, veterinary carriers for solutions, emulsions, suspensions and any other form suitable for use. The carriers which can be used include albumin, water, glucose, lactose, gum acacia, gelatin, mannitol, starch paste, saline, and other carriers suitable for use in manufacturing preparations. In addition auxiliary, stabilizing and thickening agents may be used.

The composition is administered to the fowl by an effective delivery method. Examples of delivery methods include genetic immunization as described above, aerosol delivery and parenteral administration. The dosage of effective amount of chicken interferon will depend upon the age and condition of the fowl. A daily dose typically is $2$–$10 \times 10^4$ units/kg, preferably $5 \times 10^4$ units/kg. See Sekellick and Marcus (1986), Ibid. for standard techniques for determining the unit measure for interferon.

An alternative method for preventing and/or treating viral and parasitic infection is to produce transgenic fowl where the fowl harbors an inducible gene encoding interferon endogenous to that fowl. The method of making the transgenic fowl includes the steps of introducing and incorporating recombinant DNA comprising a nucleotide sequence coding for avian interferon at an embryonic stage, preferably in the sperm, ovum, zygote or embryo, of a fowl and incubating said embryonic stage under conditions necessary for development of the fowl. Preferably, the fowl is a chicken. For example, the transgenic fowl can be prepared by incorporating the cDNA, preferably with a predetermined promoter, into a eukaryotic expression vector, for example, plasmid pcDNA3 (Invitrogen). The thus obtained plasmid DNA can then be incorporated into the desired fowl by methods generally recognized in the art. Simkiss, *Comparative Biochemistry and Physiology*, 104A:411–417, (1993); Ono et al., *Developmental Biology*, 161:126–130, (1994). Expression of the interferon in the fowl can protect the fowl from viral and/or parasitic disease.

The chicken interferon gene, generally, is operably placed behind promoters that will respond to stimuli other than the endogenous promoter for the gene. Double stranded (DS) RNA can be used to stimulate the promoter (Marcus, "In Interferon 5", Edition I, Gresser, Academic Press, pp. 115–180, 1983). A chicken metallothionein promoter can also be used (Fernando and Andrews, *Gene*, 81:177–183 (1989)), so that the cells or chickens containing this construct would respond to metal ions, such as $Cd^{++}$ or $Zn^{++}$, and produce interferon transiently, as desired.

The metal ions can be administered by any effective means, including orally or parenterally. The most preferred embodiment is oral administration. The metallic ions can be formulated in any effective composition. Suitable carriers include those described above. For example, the metallic ions can be incorporated into the fowl's feed, where ingestion of the metallic ion induces the metallothionein promoter. The effective dosage of the metallic ions can be readily determined by the skilled artisan, and depend upon the age and condition of the fowl.

The invention will be used to establish transgenic chickens that either constitutively express the chicken interferon gene, so that the chicken displays resistance to a broad spectrum of viral infections comparable to that observed in vitro, or transiently express chicken interferon as required to prevent or combat virus infection. Transiently expressed interferon is preferred because constitutive expression results in levels of interferon that might be deleterious to embryonic development. See Muller et al., *Gene*, 121:263–270 (1992) in which the early expression of the Mx'1 gene was shown to be deleterious in transgenic pigs. In activating the interferon gene system, this approach has the advantage of bringing the interferon system in to play only when required, as during outbreak of a viral disease, and not during critical developmental stages in the establishment of the transgenic chickens.

Chicken interferon expressed in this manner has the added advantage of also activating the Mx system, as it does naturally, and may render the chickens resistant to avian influenza virus as well. Avian influenza and other avian viruses can decimate flocks, and chickens that were intrinsically resistant to virus or could be activated to resistance by simply manipulating the feed would be of great commercial value. The chicken industry is a multibillion dollar industry.

Any effective method for incorporating the cDNA plasmid into the fowl can be used. Examples of such methods include microinjection, electroporation, sperm transfection, liposome fusion, and microprojectile bombardment. The desired gene can also be introduced into sperm cells by the Cornell particle gun. Microprojectile bombardment employing the Cornell particle gun was developed to deliver desired genetic constructs into cells by firing DNA-coated inert microparticles, such as tungsten into the cells. Hough and Foote, "The Effect of the Cornell Particle Gun on Bull and Rabbit Spermatatozoa", *Abs. Biol. Reprod.* Suppl. 142:65, (1990); U.S. Pat. No. 5,100,792, Sanford et al., issued Mar. 31, 1992, incorporated by reference herein.

Another method for producing transgenic chickens is using "one round" retroviral vectors. See Salter, et al., Transgenic Chickens: Insertion of Retroviral Genes into the Chicken Germ Line, *Virology*, 157:236–240 (1987), for example. It is reported that insertion of foreign DNA in early chicken embryos occurred where the DNA was injected into the yolk near the embryo in a newly laid fertile egg. The procedure employed is described in Salter et al., *Poult. Sci.*, 65:1445–1458 (1986), which is incorporated herein by reference.

It is particularly advantageous to modify the retroviral vector to improve their efficiency and reduce pathogenicity. One method which may be employed is the deletion of at least one replication gene of the retroviral vector. Crittenden and Salter, Poc. UCLA Symp., Transgenic Models in Med and Agr., pp 73–87, 1990; Salter and Crittenden, *Theor. Appl. Genetics*, 77:457–461 (1989); Crittenden, Salter and Federspiel, *Theor. Appl. Genetics*, 77:505–515, 1989; Salter and Crittenden, "Proc. Discoveries in Antisense Nucleic Acids", pp 95–110, (1989); Salter et al., *Virology*, 157:236–240, 1987; Crittenden et al., *J. Virol.*, 61:772–775, 1987; Crittenden, *Poultry Sci.*, 65:1468–1473 (1986); Crittenden, *Avian Dis.*, 30:43–46 (1986); Hughes, *Poultry Sci.*, 65:1459–1467 (1986); Salter et al., *Poultry Sci.*, 65:1445–1458 (1986); Crittenden and Salter, *Canadian J. of Animal Science*, 65:553–562 (1985); Simkiss, *Comparative Biochemistry and Physiology*, 104A:411–417, (1993); and Ono et al., *Developmental Biology*, 161:126–130, (1994).

Production of a successful transgenic chicken with non-replicating vectors has been described. Shuman, *J. of Dairy Sci.*, 72(suppl 1):61 (1989); Lee, M. R., Ph.D. Thesis, North Carolina State University, (1989); Shuman et al., *Poultry Sci.*, 67:136 (1988). None of these transgenic chickens contain the chicken interferon cDNA described herein.

In the method of this invention the DNA construct, discussed above, optionally with a suitable promoter, is impregnated in or coated on an inert microparticle. The DNA coated or impregnated microparticle is then delivered into the appropriate cell, including the sperm, ovum, zygote or embryo. Because sperm cells are natural vectors, it is preferred that the DNA coated microparticle is delivered into the sperm. It is preferred that the Cornell particle gun be employed in the delivery of the microparticle to the cell. However, any mode of effective delivery can be employed, including those described in the Sanford patent. While some loss of sperm motility may be experienced, application of a vacuum and addition of ATP may recapture some or all motility. Preferred ATP concentrations are 0.05–1.0 mM ATP.

Newly hatched chicks can be screened for the chicken interferon gene by exposing leukocytes from blood sample to $Zn^{++}$ or $Cd^{++}$ ions to induce the metallothionein promoter driven ChIFN gene.

The cDNA probe and/or the chicken interferon gene and/or any effective fragment thereof can be used as a probe to isolate the interferon gene of other avian species, fish or reptile. The method to be employed is substantially the same used and described above for isolating the chicken interferon gene.

The interferon gene so isolated can then be used, in the manner described above, for the preparation of the recombinant interferon protein or for the preparation of a transgenic animal. The recombinant interferon protein can be administered to an appropriate avian, fish or reptile in the manner described above. The administration of interferon to fish can also be accomplished, for example, by adding the interferon to the aqueous environment. The interferon may be absorbed through the gills of the fish.

Interferon can be injected into eggs to provide protection to the embryo using known techniques.

The invention will be further illustrated by the following exemplification:

EXEMPLIFICATION

Materials and Methods

Cells and Media: Monolayers of primary chick embryo cells were prepared from 10-day-old chick embryos as previously described (Sekellick and Marcus, *Methods Enzymol.*, 119:115–125, (1986); Sekellick, Biggers and Marcus, *In Vitro Cell Dev. Biol.*, 26:997–1003 (1990)). Cells were aged in vitro without a medium change for the periods of time indicated, usually 8–10 days, to enhance their IFN-inducing capacity (Sekellick and Marcus, (1986); Sekellick, Biggers and Marcus, (1990).

Source of Viruses, Preparation and Assay: The origin, growth and source of avian reovirus as well as various strains of wild-type VSV IN have been described (Winship and Marcus, *J. Interferon Res.*, 1:155–167 (1980); Sekellick and Marcus, *J. Gen. Virol.*, 70:405–415 (1989); Sekellick and Marcus, *Virology*, 95:36–47 (1979); Marcus, Sekellick & Nichol (1992); Marcus et al., *J. Interferon Res.*, 13:547–1993)). Plaque assays, stock amplification and UV radiation of avian reovirus were performed as previously described using primary chick embryo cells as host (Winship and Marcus, (1980)). VSV preparations were grown and plaqued in GMK-Vero cells as described previously (Sekellick and Marcus, (1989)).

IFN Induction and Assay: Details for the procedures used to induce and assay acid stable IFN in aged primary chick embryo cells have been described (Sekellick and Marcus (1986); Sekellick, Biggers and Marcus, (1990); Yoshida and Marcus, *J. Interferon Research*, 10:461–468, (1990)). UV-irradiated avian reovirus was used to infect primary chick embryo cells at a multiplicity of infection of 5 as described previously (Winship and Marcus, (1980)) in order to induce IFN maximally.

RNA Purification: Total cellular RNA was obtained from UV-irradiated-avian reovirus infected primary chick embryo cells at various times post infection. Cells were lysed with SDS/EDTA and total RNA extracted with water-saturated acid phenol followed by ethanol precipitation (Maniatis, Fritsch & Sambrook, *Molecular Cloning: A Laboratory Manual*(2nd Ed.), Cold Spring Harbor Laboratory Press (1989)). RNA extracted in this manner served as template in a PCR reaction or for Northern blot analysis.

Oligonucleotide Synthesis: Known mammalian IFN$\alpha\beta$ and amino acid sequences were obtained by using the Wisconsin Sequence Analysis Package, Verson 7, from Genetics Computer Group (Madison, Wis.) and were aligned to minimize gaps and maximize homology. Regions exhibiting high homology near the carboxyl end and middle of the mature protein were examined in detail at the amino acid level, and two probes were constructed based on nucleotide sequences from these regions. Nucleotide sequences were derived from amino acid sequences, favoring codon preferences observed for known chicken genes, while substituting two or more nucleotides at degenerate positions. For PCR, the "downstream" primer was anti-sense for cDNA synthesis and the "upstream" primer was sense for amplification of the cDNA with the "downstream primer". Sense and anti-sense degenerate PCR primers corresponded to nucleotide positions 307–338 and 556–575, respectively (SEQ ID NO: 1). The sense primer was a 32-mer consisting of the sequence 5'-TTGGCCATCTATGAGATGCTCCAGMANATHTT-3' (SEQ ID NO: 4). The anti-sense primer was a 20-mer consisting of the sequence 5'-CGGACCACTGTCCA NGCRCA-3' (SEQ ID NO: 5).

Polymerase Chain Reaction (PCR): RNA PCR was performed according to the protocol provided with the Perkin Elmer-Cetus Geneamp RNA PCR kit. Briefly, one microgram of total RNA isolated from primary chick embryo cells that were induced to produce interferon was used in a 20 μl reverse transcription reaction using the downstream primer for cDNA synthesis. The reaction was carried out at 42° C. for 15 minutes and then at 99° C. for 5 minutes to inactivate the reverse transcriptase. After cooling to 5° C., reaction components were added to give a 100 μl volume with both primers now present at a concentration of 0.5 μM. PCR was carried out for 35 cycles of 95° C. for 1 minute, 37° C. for 1 minute and 72° C. for 1 minute.

Purification of PCR Products: PCR products were ethanol precipitated, redissolved in water, and run out on a 3%

Nusieve GTG agarose (FMC) gel. The band of the expected size was cut from the gel, melted, and diluted 1:10 with sterile water. A 10 μl volume of this solution was used in another PCR reaction to amplify even more of the fragment so a sufficient amount was available for cloning. Reaction conditions were performed as before except the annealing was performed at 50° C. PCR products were again gel purified except the excised bands were purified from the agarose by spinning in a microfuge through Costar spin-X centrifuge filter units at 4° C. The samples were then extracted with sec-butanol to remove ethidium bromide, quantitated, ethanol precipitated and redissolved in sterile water.

Synthesis of the cDNA Fragment: The phagemid pBluescript KS(−) was cut with Eco RV to produce a blunt end and also cut with Eag I to produce a 3' overhang on the other end. The purified PCR product contained a single restriction site for Eae I toward the 5' end of the upstream primer which produced a 3' end overhang complementary to that produced by Eag I. The fragment was ligated into pBluescript under conditions favoring blunt end ligations with a molar ratio of insert:vector of 10:1. Recombinant plasmids were transformed into XL1-Blue E. Coli. Positive colonies were identified using blue/white colony selection. Recombinants were then verified by restriction digests that produced inserts of the expected size. A clone containing a 269-base insert (designated pCh269) was selected for use in subsequent studies.

DNA Sequencing of the Cloned PCR Fragment: Double-stranded DNA sequencing was performed using TAQuence Version 2.0 from USB. Plasmid was prepared from 500 ml cultures by the alkaline lysis method. Contaminating RNA was removed by lithium chloride precipitation and RNase treatment followed by organic extraction and ethanol precipitation. Plasmid was heat-denatured and flash frozen in dry ice and ethanol prior to performing sequencing reactions. Completed reactions were than analyzed on a 7% Long Ranger (J. T. Baker) polyacrylamide gel using sequencing reactions from both strands of the plasmid insert.

cDNA Cloning: Using aged primary chick embryo cells infected with UV-AVR, conditions known to produce high yields of interferon, total RNA was isolated from cells at about 8 hours post infection as described above. Poly(A)$^+$ RNA was isolated from oligo(dT)-cellulose spun columns supplied with a Pharmacia mRNA Purification Kit. cDNA was synthesized from this poly(A)$^+$ RNA and cloned into Not I-Sal I-cut plasmid pSPORT I using a Superscript Plasmid System (Gibco/BRL). Plasmid was electroporated into ElectroMAX DH10B (Gibco/BRL) cells using the "Electroporator" electroporating apparatus from Invitrogen. Clones were screened using biotinylated-PCR product prepared from pCh269 template and hybridized to DNA from colony lifts which were UV-crosslinked to MSI nylon membranes (82 mm diameter) and detected with the Colony Images Non-Isotopic Colony/Plaque Screening Kit (USB).

DNA Sequencing of cDNA Clones: Plasmids were isolated using a standard alkaline lysis method followed by ammonium acetate precipitation (for 10 ml cultures) or lithium chloride precipitation (for 500 ml cultures). This was followed by RNase treatment to remove residual contaminating bacterial RNA. The plasmids were then sequenced using the Pharmacia AutoRead Sequencing Kit for double-stranded templates with T7 and SP6 fluorescein labelled primers (supplied by the Biotechnology Center, Univ. of CT). Following termination, sequencing reactions were analyzed on the Pharmacia Automated Laser Fluorescent A.L.F. DNA sequencer using a 6% polyacrylamide gel.

Northern Blot Analysis: RNA samples were run out for 3 hours on a 1% agarose gel containing 2.2 M formaldehyde and transferred to a nylon membrane by capillary elution in 10×SSC. RNA was cross-linked to the dry membrane with 254 nm UV (0.15 J/cm$^2$). The Gibco/BRL Photogene protocol was followed for probe hybridization and nonradioactive nucleic acid detection. Hybridization solutions contained 50% formamide and reactions were performed at 42° C. Stringency washes were performed under moderate conditions using 0.1% SSC and 1% (w/v) SDS at 50° C. for 30 minutes. Membranes were exposed to Kodak XAR-5 film usually for 2–4 hours to obtain a signal of sufficient intensity.

Biological Activity of pCh132 Gene Product: pChl32 DNA was linearized with Hind III and used as template in an in vitro transcription reaction using a mCAP kit (Stratagene, La Jolla, Calif. to prepare capped mRNA with T7 RNA polymerase. Following DNase digestion, the RNA product was purified by phenol extraction and ethanol precipitation. RNA was resuspended in TE buffer for use.

pCh132 mRNA was transfected into mouse L(Y)-Clone 40 cells using Lipofectin Reagent (Gibco/BRL) as recommended by the manufacturer. Monolayers of cells in 60 mm dishes were washed 4 times with serum-free minimal essential medium (MEM) prior to addition of the Lipofectin-mRNA complex in 2 ml of serum-free MEM. Cells were incubated at 37° C. for 4–20 hours. Supernatants were stored at −20° C. prior to assay for IFN on primary chick embryo cells as described. Sekellick and Marcus, *Methods in Enzymol.*, 119:115–125 (1986).

In a separate experiment, supernatant medium from mouse L(Y)-Clone 40 cells transfected with 5 μg of RNA and collected 4 hours post transfection as described above, contained 26 units/ml of antiviral activity when tested on primary chick embryo cells. This activity was neutralized completely by incubation with a 1:25 dilution of a monoclonal antibody to ChIFN sufficient to neutralize 40–160 international units of ChIFN (Masayoshi Kohase, personal communication).

Biological expression of the ChIFN gene: Messenger RNA prepared in vitro using pCh132 DNA as template was transfected into mouse L(Y) cells and the medium tested for antiviral activity in a standard assay on chicken cells (Sekellick and Marcus, *Methods in Enzymol.*, 119:115–125, 1986) carried out in the presence or absence of monoclonal antibody specific for ChIFN. (Kohase et al., *J. Interferon Res.*, 13:S93, 1993) The highest level of antiviral activity released into the medium bathing the mouse L(Y) cells was observed 4 hours post-transfection, and decreased to one-third by 8 hours, after which time it remained constant for at least 20 hours. Cell extracts contained about 10% of the antiviral activity released by the cells. The figure shows that the activity recovered from transfected mouse L(Y) cells induced an antiviral effect in chicken cells that was proportional to the amount of mRNA added in the lipofectin-mediated transfection. This activity was neutralized by both polyclonal and monoclonal antibody specific for ChIFN. Mouse IFN was not active on chick cells, and hence the antiviral effect could not be attributed to IFN endogenously induced during the transfection process. This latter control was necessary since some plasmid preparations may be contaminated with double-stranded (ds)RNA, a potent IFN inducer. Marcus and Sekellick, *Nature*, 266:815–819 (1977).

EQUIVALENTS

Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A chicken interferon cDNA probe that comprises an at least 20-nucleotide segment of SEQ ID NO: 1, and that will bind to the complement of SEQ ID NO: 1.

2. A recombinant DNA comprising an isolated chicken interferon DNA having the nucleotide sequence shown in SEQ ID NO: 1.

3. A plasmid comprising (a) a DNA sequence coding for avian type 1 interferon having the nucleotide sequence shown in SEQ ID NO: 1; and (b) a promoter sequence operably linked to said DNA sequence.

4. A method of producing chicken interferon which comprises culturing a host cell under conditions suitable for producing chicken interferon, said host cell containing the recombinant DNA of claim 2, and recovering said chicken interferon from the cell culture.

5. The method according to claim 4 wherein said host cell is selected from the group consisting of a prokaryote, an eukaryote and a cultured mammalian cell.

6. The method according to claim 4 wherein said host cell is *Escherichia coli*.

7. The method according to claim 4 wherein said host cell is a member selected from the group consisting of insect cells and CHO cells.

8. A recombinant chicken interferon produced by the method of claim 4.

9. A recombinant chicken interferon produced by the method of claim 4 wherein said host cell is a cultured mammalian cell.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
       (A) LENGTH: 767 base pairs
       (B) TYPE: nucleic acid
       (C) STRANDEDNESS: single
       (D) TOPOLOGY: linear (ix) FEATURE:
       (A) NAME/KEY: CDS
       (B) LOCATION: 55..633

(xi) SEQUENCE DESCRIPTION: SEQ ID NO:1:

```
CGCACCACCA CCGAGCCCCA CCAGGCTCCT GCCCAGCACA ACGCGAGTCC CACC ATG       57
                                                             Met
                                                              1

GCT GTG CCT GCA AGC CCA CAG CAC CCA CGG GGG TAC GGC ATC CTG CTG      105
Ala Val Pro Ala Ser Pro Gln His Pro Arg Gly Tyr Gly Ile Leu Leu
            5                  10                  15

CTC ACG CTC CTT CTG AAA GCT CTC GCC ACC ACC GCC TCC GCC TGC AAC      153
Leu Thr Leu Leu Leu Lys Ala Leu Ala Thr Thr Ala Ser Ala Cys Asn
        20                  25                  30

CAC CTT CGC CCC CAG GAT GCC ACC TTC TCT CAC GAC AGC CTC CAG CTC      201
His Leu Arg Pro Gln Asp Ala Thr Phe Ser His Asp Ser Leu Gln Leu
    35                  40                  45

CTC CGG GAC ATG GCT CCC ACA CTA CCC CAG CTG TGC CCA CAG CAC AAC      249
Leu Arg Asp Met Ala Pro Thr Leu Pro Gln Leu Cys Pro Gln His Asn
 50                  55                  60                  65

GCG TCT TGC TCC TTC AAC GAC ACC ATC CTG GAC ACC AGC AAC ACC CGG      297
Ala Ser Cys Ser Phe Asn Asp Thr Ile Leu Asp Thr Ser Asn Thr Arg
                 70                  75                  80

CAA GCC GAC AAA ACC ACC CAC GAC ATC CTT CAG CAC CTC TTC AAA ATC      345
Gln Ala Asp Lys Thr Thr His Asp Ile Leu Gln His Leu Phe Lys Ile
             85                  90                  95

CTC AGC AGC CCC AGC ACT CCA GCC CAC TGG AAC GAC AGC CAA CGC CAA      393
Leu Ser Ser Pro Ser Thr Pro Ala His Trp Asn Asp Ser Gln Arg Gln
        100                 105                 110

AGC CTC CTC AAC CGG ATC CAC CGC TAC ACC CAG CAC CTC GAG CAA TGC      441
Ser Leu Leu Asn Arg Ile His Arg Tyr Thr Gln His Leu Glu Gln Cys
    115                 120                 125

TTG GAC AGC AGC GAC ACG CGC TCC CGG ACG CGA TGG CCT CGC AAC CTT      489
Leu Asp Ser Ser Asp Thr Arg Ser Arg Thr Arg Trp Pro Arg Asn Leu
130                 135                 140                 145

CAC CTC ACC ATC AAA AAA CAC TTC AGC TGC CTC CAC ACC TTC CTC CAA      537
His Leu Thr Ile Lys Lys His Phe Ser Cys Leu His Thr Phe Leu Gln
                150                 155                 160

GAC AAC GAT TAC AGC GCC TGC GCC TGG GAA CAC GTC GCC CTG CAA GCT      585
Asp Asn Asp Tyr Ser Ala Cys Ala Trp Glu His Val Arg Leu Gln Ala
            165                 170                 175

CGT GCC TGG TTC CTG CAC ATC CAC AAC CTC ACA GGC AAC ACG CGC ACT      633
Arg Ala Trp Phe Leu His Ile His Asn Leu Thr Gly Asn Thr Arg Thr
        180                 185                 190

TAGCCCCAAA CGCACCTCCC ACCCTTGTCC TATTTATCTA TTTATTCAAC TATTTATACA    693

AACGCCTATT TATTCTTCTA TTTATTCTTC TATTTATTCA GACAAAATAA AGCTCTCCTT    753

TTCAACACTG AAAA                                                     767
```

(2) INFORMATION FOR SEQ ID NO:2:

(i) SEQUENCE CHARACTERISTICS:
        (A) LENGTH: 162 amino acids
        (B) TYPE: amino acid
        (D) TOPOLOGY: linear (ii) MOLECULE TYPE: protein (xi) SEQUENCE DESCRIPTION: SEQ ID NO:2:

```
Cys Asn His Leu Arg Pro Gln Asp Ala Thr Phe Ser His Asp Ser Leu
 1               5                  10                  15

Gln Leu Leu Arg Asp Met Ala Pro Thr Leu Pro Gln Leu Cys Pro Gln
            20                  25                  30

His Asn Ala Ser Cys Ser Phe Asn Asp Thr Ile Leu Asp Thr Ser Asn
        35                  40                  45

Thr Arg Gln Ala Asp Lys Thr Thr His Asp Ile Leu Gln His Leu Phe
    50                  55                  60

Lys Ile Leu Ser Ser Pro Ser Thr Pro Ala His Trp Asn Asp Ser Gln
 65                  70                  75                  80

Arg Gln Ser Leu Leu Asn Arg Ile His Arg Tyr Thr Gln His Leu Glu
                85                  90                  95

Gln Cys Leu Asp Ser Ser Asp Thr Arg Ser Arg Thr Arg Trp Pro Arg
            100                 105                 110

Asn Leu His Leu Thr Ile Lys Lys His Phe Ser Cys Leu His Thr Phe
        115                 120                 125

Leu Gln Asp Asn Asp Tyr Ser Ala Cys Ala Trp Glu His Val Arg Leu
    130                 135                 140

Gln Ala Arg Ala Trp Phe Leu His Ile His Asn Leu Thr Gly Asn Thr
145                 150                 155                 160

Arg Thr
```

(2) INFORMATION FOR SEQ ID NO:3:

(i) SEQUENCE CHARACTERISTICS:
        (A) LENGTH: 269 base pairs
        (B) TYPE: nucleic acid
        (C) STRANDEDNESS: single
        (D) TOPOLOGY: linear (ii) MOLECULE TYPE: cDNA to mRNA (xi) SEQUENCE DESCRIPTION: SEQ ID NO:3:

```
TTGGCCATCT ATGAGATGCT CCAGCAGATT TTCAAAATCC TCAGCAGCCC CAGCACTCCA      60
GCCCACTGGA ACGACAGACG CGAACGCCAA AGCCTCCTCA CACCGGAGTC CACCGCTACA     120
CCAGACCTGA GCAATGCTTG GACAGCAGAG ACACGCTCTC CGGACGCGAT GGCCTCGCAA     180
CCTTCACCTC ACCATCAAAA AACACTTCAG CTGCCTCCAC ACCTTCCTCC AAGACAACGA     240
TTACACGCCT GCGCTTGGAC AGTGGTCCG                                      269
```

(2) INFORMATION FOR SEQ ID NO:4:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:4:

```
TTGGCCATCT ATGAGATGCT CCAGMANATH TT                                   32
```

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:5:

CGGACCACTG TCCANGCRCA          20

(2) INFORMATION FOR SEQ ID NO:6:

(i) SEQUENCE CHARACTERISTICS:
        (A) LENGTH: 193 amino acids
        (B) TYPE: amino acid
        (D) TOPOLOGY: linear (ii) MOLECULE TYPE: protein (xi) SEQUENCE DESCRIPTION: SEQ ID NO:6:

```
Met Ala Val Pro Ala Ser Pro Gln His Pro Arg Gly Tyr Gly Ile Leu
 1               5                  10                  15

Leu Leu Thr Leu Leu Leu Lys Ala Leu Ala Thr Thr Ala Ser Ala Cys
                20                  25                  30

Asn His Leu Arg Pro Gln Asp Ala Thr Phe Ser His Asp Ser Leu Gln
                35                  40                  45

Leu Leu Arg Asp Met Ala Pro Thr Leu Pro Gln Leu Cys Pro Gln His
        50                  55                  60

Asn Ala Ser Cys Ser Phe Asn Asp Thr Ile Leu Asp Thr Ser Asn Thr
65                  70                  75                  80

Arg Gln Ala Asp Lys Thr Thr His Asp Ile Leu Gln His Leu Phe Lys
                85                  90                  95

Ile Leu Ser Ser Pro Ser Thr Pro Ala His Trp Asn Asp Ser Gln Arg
                100                 105                 110

Gln Ser Leu Leu Asn Arg Ile His Arg Tyr Thr Gln His Leu Glu Gln
                115                 120                 125

Cys Leu Asp Ser Ser Asp Thr Arg Ser Arg Thr Arg Trp Pro Arg Asn
        130                 135                 140

Leu His Leu Thr Ile Lys Lys His Phe Ser Cys Leu His Thr Phe Leu
145                 150                 155                 160

Gln Asp Asn Asp Tyr Ser Ala Cys Ala Trp Glu His Val Arg Leu Gln
                165                 170                 175

Ala Arg Ala Trp Phe Leu His Ile His Asn Leu Thr Gly Asn Thr Arg
                180                 185                 190

Thr
```